United States Patent [19]
Wohlstein et al.

[11] Patent Number: 5,296,843
[45] Date of Patent: Mar. 22, 1994

[54] FLUID OR VAPOR DIAGNOSTIC DEVICE

[75] Inventors: Scott D. Wohlstein, Convent Station; Emil W. Ciurczak, Morristown, both of N.J.

[73] Assignee: SD Laboratories, Inc., Convent Station, N.J.

[21] Appl. No.: 677,643

[22] Filed: Mar. 28, 1991

[51] Int. Cl.$^5$ .............................................. G08B 21/00
[52] U.S. Cl. .................... 340/603; 340/438; 250/573; 250/575; 356/70; 356/320; 356/436
[58] Field of Search ................ 340/603, 619, 438; 250/573, 575; 356/70, 319, 320, 436

[56] References Cited

U.S. PATENT DOCUMENTS

| | | | |
|---|---|---|---|
| 3,927,944 | 12/1975 | Iwahashi et al. | 356/97 |
| 4,227,811 | 10/1980 | Tohyama et al. | 356/325 |
| 4,300,689 | 11/1981 | Franklin et al. | 209/524 |
| 4,350,441 | 9/1982 | Wicnienski | 356/40 |
| 4,534,651 | 8/1985 | Minikane | 356/440 |
| 4,570,069 | 2/1986 | Gager | 250/343 |
| 4,649,711 | 3/1987 | Sibley et al. | 62/129 |
| 4,699,509 | 10/1987 | Kamiya et al. | 356/70 |
| 4,707,133 | 11/1987 | Roberts et al. | 356/320 |
| 4,755,048 | 7/1988 | Kaufman | 356/407 |
| 4,911,549 | 3/1990 | Karkar | 356/39 |
| 4,929,847 | 5/1990 | Yamazoe et al. | 356/70 X |

*Primary Examiner*—Jeffrey Hofsass
*Attorney, Agent, or Firm*—Curtis D. Kinghorn

[57] ABSTRACT

A device is provided which passes light of preselected wavelengths through a fluid or vapor to be tested. The light is detected after it has passed through the fluid or vapor. Upon detection, a voltage is created which is proportional in amplitude to the detected light strength for each wavelength of light. These voltages are compared to produce a ratio which represents the condition of the fluid or vapor which is tested. When the ratio is outside of preselected boundaries, control signals are generated which may trigger alarms or otherwise respond to the condition.

26 Claims, 3 Drawing Sheets

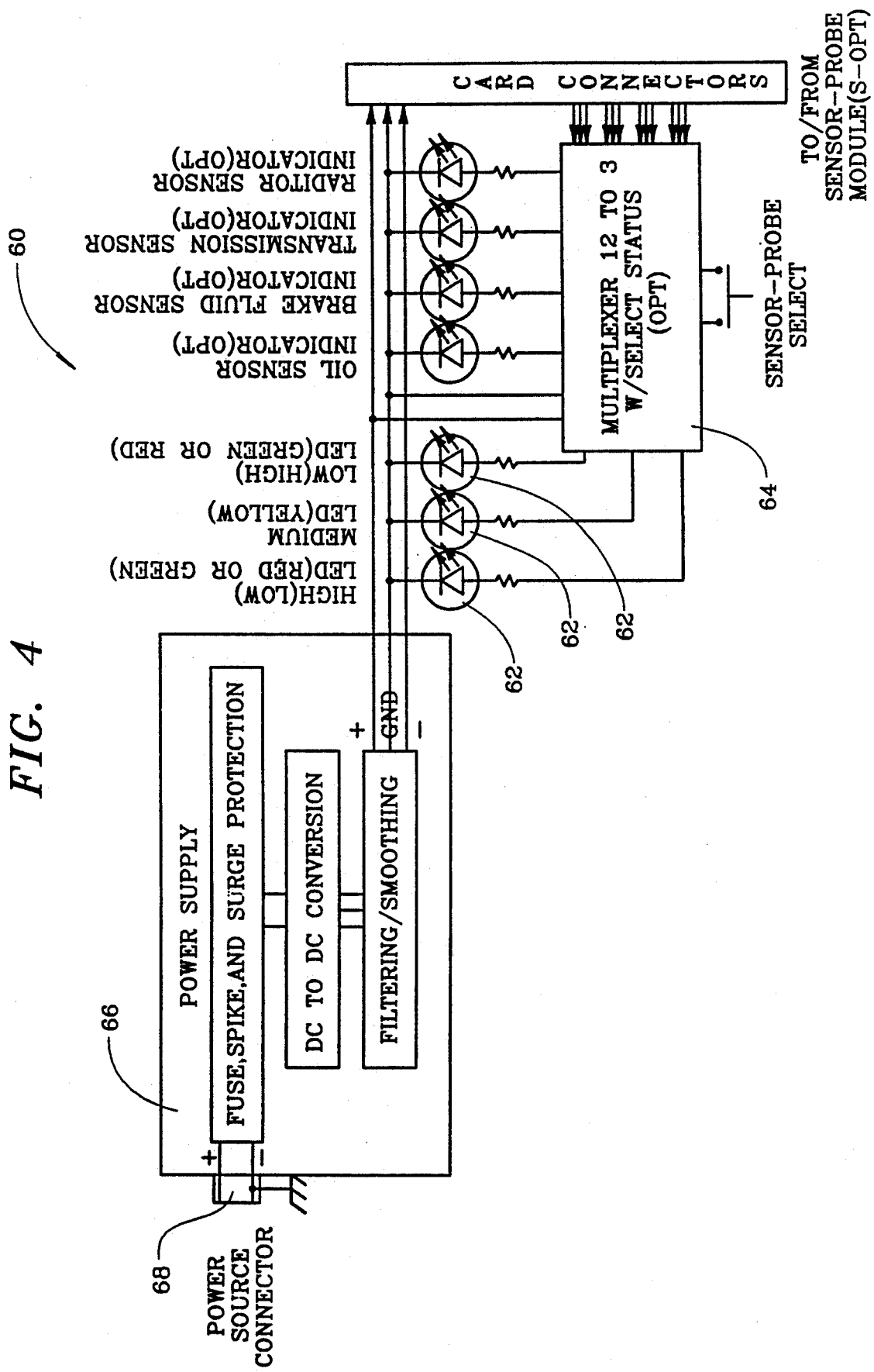

FLUID OR VAPOR DIAGNOSTIC DEVICE

FIELD OF THE INVENTION

The instant invention relates to a fluid or vapor diagnostic device and more particularly to a device which non-destructively determines the quality of a fluid or vapor tested by passing light of different wavelengths through the fluid or vapor and then comparing the ratio of the resulting detected light strength to a predetermined ratio indicating whether the fluid's or vapor's operating parameters are within acceptable limits.

BACKGROUND OF THE INVENTION

It has been found that when many fluids are exposed to a variety of environmental conditions, their physical properties change. These changes occur primarily in two areas. The chemical composition of the fluid itself may be changed through the application of heat, pressure, chemical reactions with other fluids, or air-oxidation. In addition, the fluid may be contaminated by other fluids, contaminants or particulate matter from other sources, which, although not chemically combining with the fluid, affects the fluid's ability to function as it was intended, which function is best accomplished by a pure fluid.

Exemplary of such a fluid susceptible to both of these changes is lubricating motor oil used in an internal combustion engine. A pure motor oil is ideally suited for providing lubrication within the internal combustion engine. However, due to the high temperature necessarily present in such engines, breakdown of the molecular structure of the motor oil takes place with resulting loss of lubricating ability. The remnants of the broken down motor oil molecules remain in the motor oil as contaminants. In addition, other contaminants such as carbon deposits and fine metal particles which result from the operation of the engine are also introduced into the motor oil thereby contaminating it. Other contaminants are introduced into the motor oil such as water or antifreeze from the engine cooling system. Dust particles, introduced into the engine with the air through the carburization system, are blown past compression and oil rings into the engine crank case from the combustion chamber during the compression stroke of the pistons.

Given time, the breakdown of pure motor oil and the introduction of contaminants into the motor oil renders the motor oil unable to effectively perform its job of lubricating the engine parts. When this occurs, the used motor oil should be replaced with new motor oil. The amount of time it takes for motor oil to reach this condition depends on a variety of factors including the strain put on the engine, the adequacy of cooling measures related to the engine, and external environment of the engine during operation.

Many fluids have additives added to them to enhance their inherent capabilities. These additives result in variant chemical and light absorbing properties. Examples of such chemicals are the various types of fuel enhancers used in the automotive fuel industry. For example, the introduction of ethanol, a common additive in many fuels, radically changes in a predictable way the overall light absorption properties of the resultant ethanol gasoline mixture.

The instant invention was designed to detect both when a fluid, either by breakdown or by contamination, has moved outside of an acceptable range of operating parameters, and also when the presence of certain additives are present in the tested fluid.

In researching these two problems, it was discovered that the light absorbing properties of a fluid is altered by the breakdown of the fluid itself, or by the introduction of contaminants or additives into the fluid. It was also discovered that breakdown or contamination of the fluid affects the light absorbing characteristics of the fluid by different amounts for different wavelengths of light. In particular, it was found that a ratio established by passing light of various wavelengths through the fluid to be tested and then detecting and comparing the strength of the light after passing through the fluid indicates the condition of the fluid related to the above mentioned detrimental characteristics. In particular, it was found that when the ratio for the preselected wavelengths reaches a certain ratio, the fluid is no longer within acceptable standards set for the fluid. With this in mind, the instant invention was motivated.

Because the change in fluid takes place within the environment where the fluid is found and because change in the fluid is a continuous process, the fluid should be tested continuously while it is being used in order to immediately detect detrimental changes. In this context, it is preferable to non-destructively, continuously test the fluid so that the testing process itself does not contribute to the breakdown and contamination problems of the fluid. Therefore, the light of various wavelengths should be introduced to the fluid in such a way that it can continuously and non-destructively interact with the fluid while helping to determine the condition of the fluid.

SUMMARY OF THE INVENTION

Light of preselected wavelengths is passed through a fluid to be tested. The light is detected after passing through the fluid. Thereafter, a voltage is created for each wavelength of light, proportional in amplitude to the detected light strength of each wavelength. These proportional voltages are compared to produce a ratio which represents the condition of the fluid. When the ratio is outside a preset acceptable limit, control signals, which may trigger alarms or other warning devices, are triggered.

The light of the selected wavelengths is created preferable by appropriate photodiodes. The light is introduced into the fluid to be tested by transmitting the light of the various frequencies through respective fiber optic cables into a reservoir of the fluid. There the light is emitted across a gap through which the fluid may travel. The emitted light is then received through a corresponding fiber optic cable on the other side of the gap. The received light is transmitted through a fiber optic cable out of the reservoir where its strength may be determined.

The signal strength of the light received across the gap is determined by having the light impinge on a detector which produces a voltage output proportional to the impinging light strength. The resulting electronic analog signal may be processed to amplify it and filter noise present with the signal. Thereafter, the electronic signals corresponding to the detected light strengths from the different wavelengths are electronically combined to from a ratio. This ratio has been found to represent the quality of the fluid that is being tested.

The ratio is analyzed to determine whether it lies within preselected boundaries representing acceptable qualities of the fluid. If the ratio is found to be outside of these boundaries, control signals are generated to draw attention to the unacceptable quality of the fluid.

In the preferred embodiment, a probe containing the light emitting and receiving fibers, as well as the gap between them, is mounted in the wall of a reservoir of a fluid to be tested. The light creating devices, the light detectors, ratio determining and analyzing circuitry, control signal generator circuitry, and alarm means are all located outside the fluid reservoir.

In an alternate embodiment, a handheld unit having a probe comprising respective input and output fiber optics separated by a gap is provided. The probe may be immersed into a selected fluid for testing. In this embodiment, the operation of the device is exactly the same as that described above except that the gap and fiber optic cords are not continuously present within the fluid reservoir to be tested, but are instead inserted into the fluid at the discretion of the user.

It is an object of the invention to provide a device for non-destructive testing of fluids and vapors in real time in the environment where the fluids and vapors are found under work conditions.

It is another object of the invention to provide a device which non-destructively tests the conditions of the fluid or vapor by determining the amount of light transmitted through the fluid or vapor.

It is another object of the invention to provide a device which non-destructively analyzes the composition of the fluid or vapor to be tested by comparing the ratios of light of varying wave lengths after it has been passed through the fluid to be tested.

It is a further object of the invention to alert the operator when the ratio of the strength of light of varying wavelengths after being passed through the fluid to be tested indicates that the operating parameters of the fluid are outside a preselected range of values.

It is another object of the invention to provide a device which may be mounted in contact with the fluid to be tested to continuously monitor the condition of the fluid.

It is yet another objective of the invention to provide a device which is inexpensive to manufacture and simple to build.

These and other objectives of the invention will become clear from the foregoing and from the following Detailed Description of the invention.

BRIEF DESCRIPTION OF THE DRAWINGS

FIG. 4 is a block diagram of the preferred embodiment of the signaling system.

DETAILED DESCRIPTION OF THE PREFERRED EMBODIMENT

Figure 1:
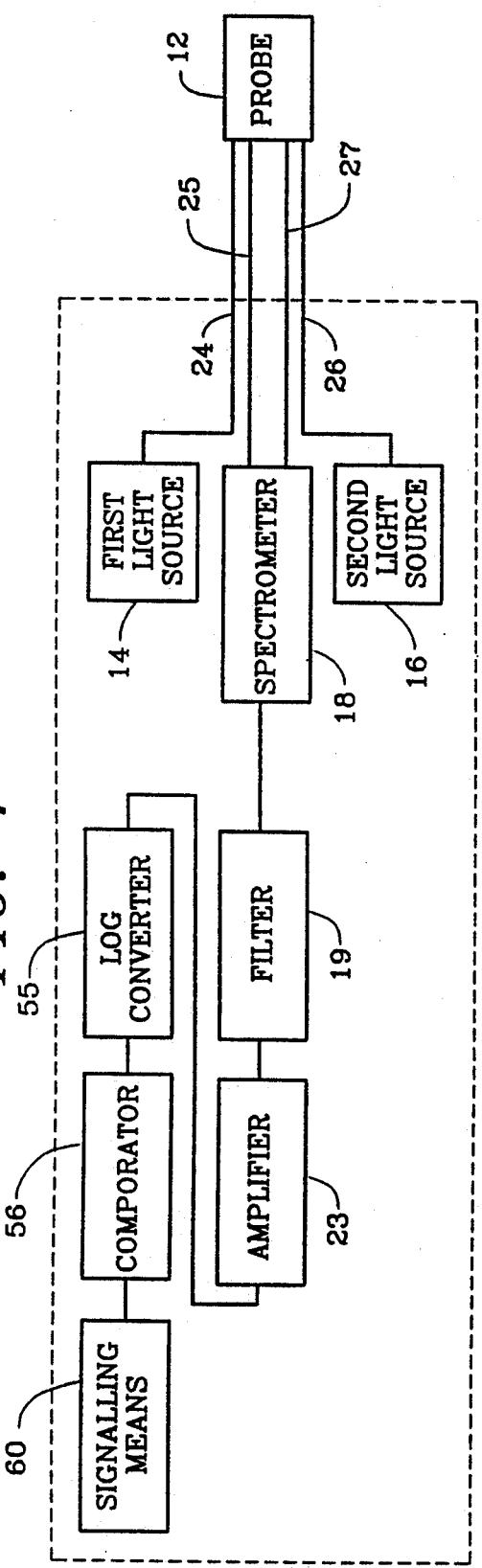
FIG. 1 is a block diagram of the invention.

FIG. 1 shows a block diagram of the invention generally labeled 10. A probe 12 (FIG. 2A, B) is placed in contact with the fluid or vapor to be tested. First and second light sources 14, 16, (FIG. 3) respectively, each provide light of a preselected wavelength to probe 12 through first and second input cables 24, 26 respectively. Preferably, first and second light source 14, 16 are photo-diodes while first and second input cable 24, 26 are fiber optic cables.

In the preferred embodiment the photo-diodes are chosen to have specific emission frequencies for the particular fuel to be analyzed. These preselected wavelengths have been experimentally determined to yield optimum results in determining the quality of the fluid that is tested. Experience has shown that for most fluids, the wavelength of light used ranges from 0.4 micrometers, which is in the visible range, to 5 micrometers which is in the mid-infrared range.

In analyzing ordinary motor oil, for example, it has been found that wavelengths of 450 nm and 550 nm yield the most accurate determination of the quality of the motor oil. Alternately, in analyzing JP-10 jet fuel vapors, the fuel used in missile and rocket propulsion, the wavelength of 1500 nm has been found to be particularly effective.

Although photo diodes are the preferred light source 14,16 for the instant invention, any other source of light which is able to produce selected wavelengths such as standard LEDs, SRLEDs, or laser diodes are within the scope of the invention. Additionally, lasers at the preselected wavelengths, monochromatic incandescent light sources, or filtered light which produces light at the preselected wavelengths may also be used. These examples are merely exemplary and not intended to be limiting. The important thing is that light, including possibly modulated light, of preselected wavelengths is made available. The preselected wavelengths may be either fixed wavelengths or preselected bands of wavelengths which may be scanned.

Figure 2B:
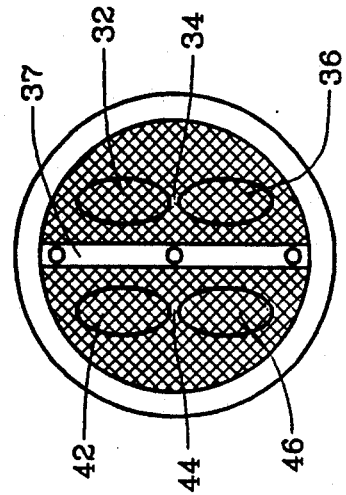
FIG. 2B is a plan view of the probe.
Figure 2A:
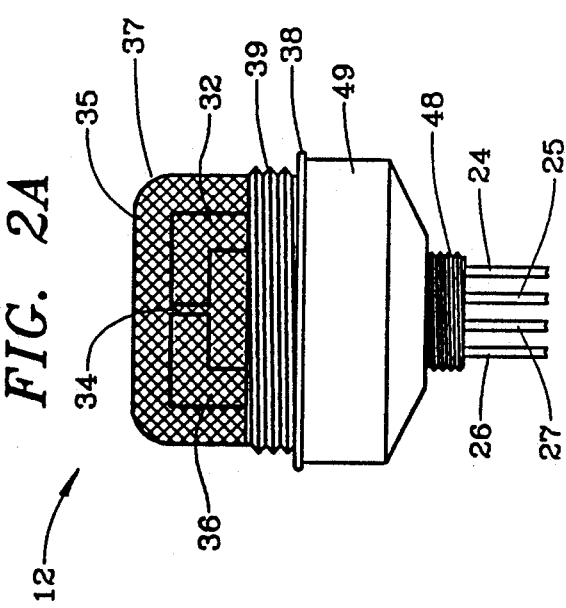
FIG. 2A is a side view of the probe.
Figure 3:
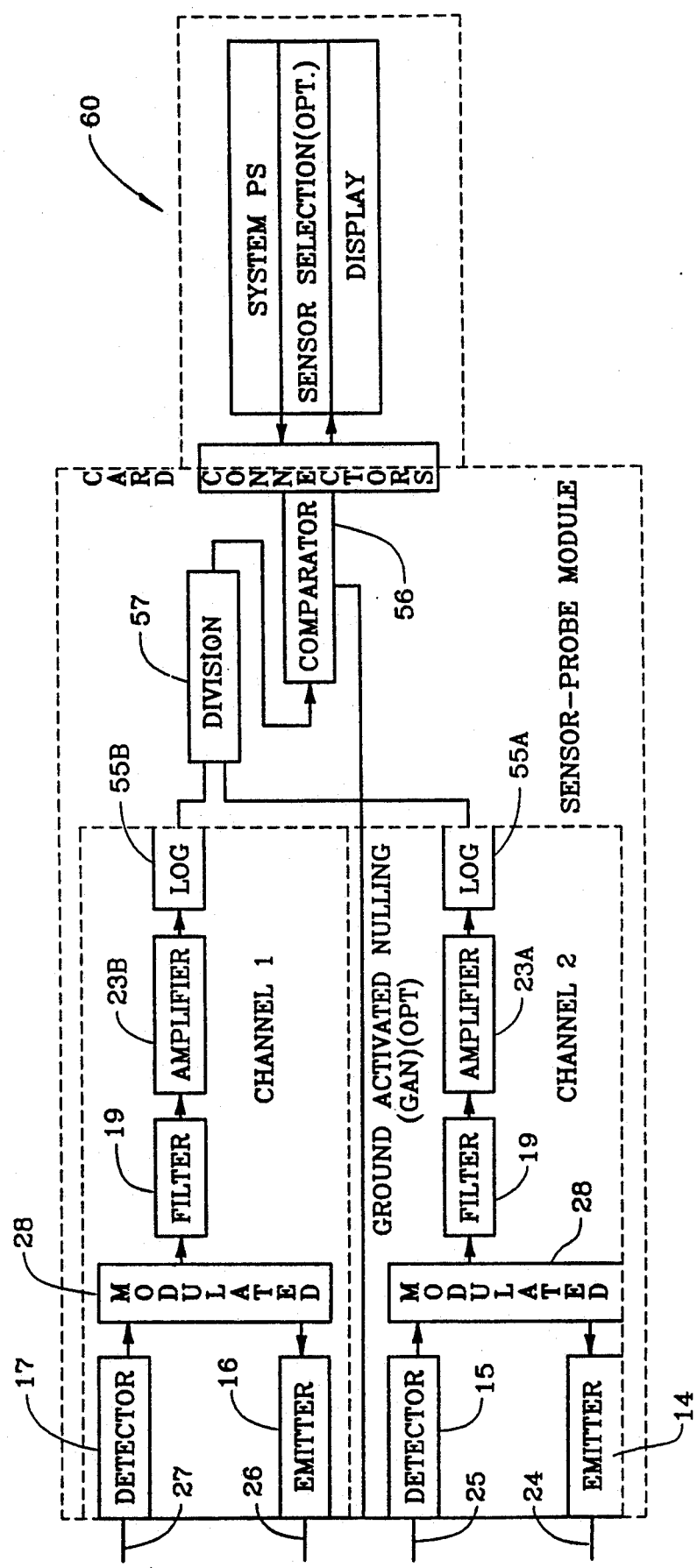
FIG. 3 is a block diagram of the electronics of the invention.

First and second input cables 24 26 are attached on their opposite ends to probe 12 as shown in detail in FIG. 2A. Cables 24, 26 are fiber optic cables. As can be seen, the first and second input cables 24, 26, enter probe 12 through a connector 48. Connector 48 is in turn attached to bulk head 49. The fiber optic cables of first and second input cables 24 and 26 extend through connector 48 and bulk head 49 and exit bulk head 49 through first and second emission fibers 36, 46, respectively which are also fiber optic cables.

Also extending out of the end of bulk head 49 are first and second detection fibers 32, 42 also comprised of fiber optic cables. In the preferred embodiment, each light source has its own fiber optic cable carrying that light to and from the fluid reservoir. A first and second gap 34, 44 separates the emission fibers 36, 46 and detection fibers 32, 42 respectively. First and second gaps 34, 44 allow the fluid or vapor of interest to move between the respective emission fibers 36, 46 and detection fibers 32, 42. Depending on the fluid to be analyzed, the gap 34,44 between respective emission and detection fibers 36,32 and 46,42 may be quite small, possibly even being as small as a millimeter. Table 1 shows the length of the gap 34, 44 found to be most effective in analyzing the corresponding fluid or vapor with the respective wavelength of light. Also shown is the type of analysis possible and whether the analysis is qualitative or quantitative.

TABLE 1

| FLUID/VAPOR | WAVE-LENGTH RANGE | GAP LENGTH | TYPE OF ANALYSIS |
|---|---|---|---|
| Oil base lubricant (fluid) | 400–700 nm | 1–20 mm | Qualitative |
| Hydraulic Oil (fluid) | 400–700 nm | 1–20 mm | Qualitative |
| Brake fluid (fluid) | 400–700 nm | 1–20 mm | Qualitative |
| Transmission fluid (fluid) | 400–700 nm | 1–20 mm | Qualitative |

TABLE 1-continued

| FLUID/VAPOR | WAVE-LENGTH RANGE | GAP LENGTH | TYPE OF ANALYSIS |
|---|---|---|---|
| Coolant or Radiator (fluid) | 400–700 nm | 1–20 mm | Qualitative |
| Organic, Carbon based Fuel (vapor) (Example-gasoline) | 800–2000 nm | 10–20 cm | Quantitative |
| Organic, Carbon based Solvents (vapor) | 800–2000 nm | 10–20 cm | Quantitative |

First and second detection fibers 32, 42 extend through bulk head 49 and connector 48 to exit probe 12 through first and second output cables 25, 27 respectively. Output cables 25, 27 are also made of fiber optics, and are connected to spectrometer 18.

A screen 35 surrounds first and second emission fibers 36,46 and first and second detection fibers 32,42. This screen 35 prevents debris from entering first and second gaps 34,44 and disrupting the light path between the respective emission and detection fibers. In addition, a wall 37, shown in side view in FIG. 2A and in top view in FIG. 2B, is placed between the respective pairs of emission and detection fibers 36,32 and 46,42. This wall 37 prevents stray light from one of the emission fibers 36,46 from being diffracted into the other pair's detectors 42,32 and thereby affecting the light signal detected across respective first and second gaps 34,44.

Spectrometer 18 comprises detectors 15, 17 and analyzes the absolute strength or intensity of the light received from first and second detection fibers 32, 34 which has been passed on to spectrometer 18 through first and second output cables 25, 27. Spectrometer 18 determines this absolute light strength for each frequency of light received from the respective first and second detection fibers 32,34. In essence, spectrometer 18 converts the light signals of varying amplitude into a proportional electric signal of varying electrical amplitude. Cadmium sulfide (CdS) or Lead Sulfide/Lead Selenium (PbS/PbSe) detectors 15, 17 have been found to be particularly adapted to perform this conversion.

Because two wavelengths of light are passed through the fluid to be tested, and because the light of different frequencies interact with the fluid differently, it is desirable to avoid having light at one wavelength scattered through the fluid into the detector corresponding to the other wavelength. This unwanted scattering is avoided by alternately "pulsing" or activating the respective light emitters 14,16 and simultaneously activating the corresponding detectors 15, 17 within spectrometer 18. This "pulsing" is done by modulator 28 which is a timer connected to a switch which alternately activates and deactivates the respective light emitters 14, 16 and corresponding detectors 15, 17. An RCA-LM555CN timer and GE-CD4066 Quad-Bilateral Switch have been found to produce an excellent modulator 28. In this way, any scattered light of one wavelength which may be received by the other wavelength's fiber optic cables due to scattering through the fluid, impinges on an inactive detector. Because the detectors 15, 17 is inactivated by modulator 28, no "false" reading for the non-activated wavelength is created. Additionally, the "pulsing" or modulation of the emitters and detectors helps eliminate noise and drift, whether electronically or environmentally induced, which has been found to be present in long term, precision measurements.

After electrical signals corresponding in strength to the light received by respective first and second detection fibers 32,34 has been determined, the analog voltage signal produced by each detector is filtered through filter 19 to improve the signal quality. Filter 19 may be any analog or digital voltage filter which suppresses spurious noise in the voltage signal from the detectors. For example, filter 19 may include an A to D converter followed by a digital filter followed in turn by a D to A converter. As another example, filter 19 may include a phase locked loop. Such filters are well known in the art. The resulting filtered signal is now a "clean" signal free of spurious noise.

This "clean" signal may be amplified by amplifiers 23 A,B to produce an appropriate signal strength as needed. The amplifiers 23 may be standard OP-AMPs. The outputs of amplifiers 23, A, B are passed to Log converters 55A, B which determine the Log of each wavelength's signal strength. Log converters 55A, B are diode feedback type Log converters or Log/Antilog Amps such as GE-1CL8048 which are well known in the art.

The outputs from Log converters 55A, B are then divided by Analog Divider 57 to produce a voltage based on the ratio of the outputs of amplifiers 23A, B. This voltage is indicative of the fluid quality. Analog divider 57 may be an analog divider/Multiplier such as the Burr-Brown MPY100AG. This establishes the ratio of the determined Logs according to the formula:

$$\text{Ratio} = \frac{\text{Log (Signal Strength of Wavelength 1)}}{\text{Log (Signal Strength of Wavelength 2)}}.$$

In another embodiment, a central processing unit may be appropriately connected to the outputs of amplifiers 23A, B to calculate, according to preprogrammed instructions, the ratio of voltages and produce a voltage or digital signal indicative of the ratio.

In the preferred embodiment, and in the alternate embodiment where a voltage representative of the ratio is produced, when the ratio and consequently voltage moves outside of preselected values, control signals are generated. The determination that the ratio is outside the preselected values is done by a comparator stage generally labeled 56. Comparator 56 may be a dual OP AMP or part of as standard Quad OP AMP configured to operate in a window.

In the alternate embodiment containing a central processing unit, the determination that the ratio is outside of the preselected values and the generation of control signals may be done by the central processing unit in response to preprogrammed instructions.

These control signals in turn activate signaling mean 60 for alerting the operator that the fluid has moved outside the range of acceptable operating parameters. These signaling means 60 include, in the preferred embodiment (FIG. 4), LED's 62, activated through a multiplexer 64 connected to comparator 56, which visually indicate that the fluid is outside the acceptable operating parameters. Alternatively, or in addition, an audio alarm, or additional visual alarm means such as flashing lights, as well as the possibility of interacting with a computerized control system may also be used.

In the preferred embodiment, bulk head 49 also includes threads 39 which allow probe 12 to be inserted into the wall of a container containing a reservoir of the fluid or vapor to be tested. O-ring 38 is seated in bulk head 49 so that probe 12 will be in sealing contact with the wall of the container containing the fluid or vapor to be tested. Fiber optic input cables 24, 26 from the light sources 14, 16 themselves may then be attached to the appropriate fiber optic cables of the probe 12, or the light sources 14, 16 may themselves be attached to the ends of fiber optic cables of the probe 12.

Also in the preferred embodiment, a power supply 66 (FIG. 4) is provided which is connected to an alternating current source 68 such as a wall socket. Power supply 66 converts alternating current to direct current for powering the electronic components of the device 10 by means well known in the art.

In an alternate embodiment, a handle may be attached to bulkhead 49 to allow for manual placement of the probe 12 directly into a fluid or vapor to be tested. This embodiment of the invention will be particularly suited for testing samples of fluid in a spot-check fashion. In this embodiment, the spectrometer 18, filter 19, log converters 55, comparator 56, analog divider 57 and signaling means 60, as well as first and second light source 14, 16 may all be contained in a single portable unit which is connected to probe 12 by first and second input and output cables 24, 26 and 25, 27, respectively. In this embodiment, power supply 66 is preferably a battery to render the device 10 more portable. However, the power supply of the preferred embodiment may also be used in this embodiment.

While the instant invention has been described in relation to fluids, it works equally well when addressed to the analysis of vapors. When used in this context, vapors instead of fluid is present in the gap 34,44 between the fiber optic cables.

While the instant invention has been described in what is considered to be the preferred embodiment, as well as alternative embodiments, it is to be understood that these descriptions are given by means of example only, and not by means of limitation. It is to be understood that changes and modifications may be made to the description given and still be within the scope of the invention. Further, it is clear that obvious changes and modifications will occur to those skilled in the art.

What I claim is:

1. A non-destructive diagnostic device for continuously testing fluid or vapor contained in a fluid or vapor reservoir comprising:
   a) at least two light sources, each of said light sources emitting light at a different preselected wavelength;
   b) means for directing light from each of said light sources through the fluid or vapor;
   c) means for receiving light from each of said light sources after it has been directed through the fluid or vapor,
   d) means for positioning said means for directing light and said means for receiving light in the fluid or vapor reservoir, said means for receiving light separated from said means for directing light by a distance, thereby forming a gap through which the fluid or vapor may pass;
   e) means, connected to said means for receiving light, for determining the absolute intensity of light from each of said light sources after the light has been directed through the fluid or vapor in the reservoir and passed to said means for determining through said means for receiving;
   f) means for determining the ratio of absolute intensity of light from each of said light sources after the light has been directed through the fluid or vapor;
   g) means, responsive to said means for determining, for creating a control signal indicating that said ratio is outside of a preselected limit; and,
   h) means, responsive to said control signal, for communicating that said ratio is outside of said preselected limit.

2. The device of claim 1, wherein said light sources are chosen from a group consisting of photodiodes, light emitting diodes, laser diodes, SRLEDs, lasers, and monochromatic incandescent light bulbs.

3. The device of claim 1, wherein said light sources comprise means for creating monochromic light.

4. The device of claim 1 wherein said means for directing light comprises input fiber optic cables receiving light from respective said light sources at one end and directing said light through the fluid or vapor at the other end.

5. The device of claim 1 wherein said means for receiving light comprises output fiber optic cables, said output fiber optic cables each receiving at one end light directed through the fluid or vapor from said respective means for directing light, and passing said light to respective said means for determining at the other end of said output fiber optic cables.

6. The device of claim 1 further comprising a probe, said probe being insertable into the fluid or vapor to be tested, said means for directing light including respective fiber optic input cables connecting each of said light sources with the fluid or vapor to be tested, said means for receiving light also including respective fiber optic output cables extending from the fluid or vapor to be tested to respective said means for determining the absolute intensity, said input and output cables extending into and out of, respectively, said probe, respective said input and output cables corresponding to each of said light sources, respective said input and output cables being separated from each other within said probe thereby forming said gap, each of said gaps in contact with the fluid or vapor whereby fluid or vapor to be tested may move though each of said gaps between said input and output cables so that light from said each of said respective light sources travels through its respective said input cable, through its respective said gap, and through its respective said output cable before impinging on respective said means for determining the absolute intensity.

7. The device of claim 1, wherein said means for determining the absolute intensity of light from each of said light sources after it has been directed through said fluid comprises a spectrometer.

8. The device of claim 7 wherein said spectrometer includes detectors for detecting the light chosen from a group consisting of cadmium sulfide (Cds) detectors and Lead Sulfide-Lead Selenium (pbS/PbSe) detectors.

9. The device of claim 1, wherein said means for determining the ratio of absolute intensity of light comprises an analog divider.

10. The device of claim 1, wherein said means for creating control signals includes a central processing unit electronically connected to said means for determining the ratio of absolute intensity of light, said central processing unit programmed to generate a control signal when said ratio of absolute intensity of light is determined by said central processing unit to be outside of a range of operating parameters preprogrammed into said central processing unit.

11. The device of claim 1 further comprising means for modulating said light sources.

12. The device of claim 11 wherein said means for modulating said light sources comprises means for alternately pulsing respective said light sources and simultaneously activating the corresponding said means for determining the absolute intensity of light so that light from one light source that is diffracted by the fluid or vapor will impinge on an inactive means for determining the absolute intensity of light corresponding to an inactive said light source.

13. The device of claim 1 wherein said gap has a width of between 1 and 20 millimeters when a fluid is passed through said gap and a width of between 10 and 20 centimeters when a vapor is passed through said gap.

14. A non-destructive diagnostic device for continuously testing fluid or vapor contained in a fluid or vapor reservoir comprising:
 a) at least two light sources, each of said light sources emitting light at a different preselected wavelength;
 b) means for directing light from each of said light sources through the fluid or vapor comprising respective input fiber optic cables, said input fiber optic cables receiving light from said light sources at a first end and directing the light through the fluid or vapor at a respective second end;
 c) means for receiving light from each of said light sources after it has been directed through the fluid or vapor comprising respective output fiber optic cables, each having a first and 15. The device of claim 14, wherein said means for creating control signals includes a central processing unit electronically connected to said means for determining the ratio of absolute intensity of light, said central processing unit programmed to generate a control signal when said ratio of absolute intensity of light is determined by said central processing unit to be outside of a range of operating parameters preprogrammed into said central processing unit.

16. The device of claim 14 further comprising a probe, said probe being insertable into the fluid or vapor to be tested, said probe enclosing respective said second ends of said input fiber optic cables and said first end of said output fiber optic cables, said second end of said input fiber optic cables and said first end of said output fiber optic cables being separated thereby forming said gap through which the fluid or vapor may pass whereby fluid or vapor to be tested may move through each of said gaps between said input and output cables so that light from each of said respective light sources travels through its respective said input cable, through its respective said gap, and through its respective said output cable before impinging on respective said spectrometer.

17. A non-destructive diagnostic device for continuously testing fluid or vapor comprising:
 a) at least two photo diodes, each of said photo diodes emitting light at a different preselected wavelength;
 b) means for directing light from each of said photo diodes through the fluid or vapor comprising respective input fiber optic cables, said input fiber optic cables receiving light from respective said light sources at a first end and directing the light through the fluid or vapor at a respective second end;
 c) means for receiving light from each of said photo diodes after it has been directed through the fluid or vapor comprising respective output fiber optic cables, each having a first and a second end, respective said output fiber optic cables each receiving light directed through the fluid or vapor from respective said input fiber optic cables at said first end, respective said input fiber optic cables separated from respective said output fiber optic cables by a distance, thereby forming a gap through which the fluid or vapor may pass, said gap having a width of between 1 and 20 millimeters when a fluid is passed through said gap and a width of between 10 and 20 centimeters when a vapor is passed through said gap;
 d) means, connected to said second end of respective said output fiber optic cables, for determining the absolute intensity of light from each of said photo diodes after the light has been directed through the fluid or vapor, said means for determining comprising a spectrometer, whereby each of said light sources has a corresponding means for directing light and a means for receiving light;
 e) means for determining the ratio of absolute intensity of light from each of said photo diodes after the light has been directed through the fluid or vapor, comprising an analog divider;
 means, responsive to said means for determining, for creating control signals indicating that said ratios are outside of preselected limits;
 g) means, responsive to said control signals, for communicating that said ratios are outside of preselected limits; and
 h) a probe, said probe being insertable into the fluid or vapor to be tested, said probe enclosing respective said second ends of said input fiber optic cables and said first end of said output fiber optic cables, said second end of said input fiber optic cables and said first end of said output fiber optic cables being separated thereby forming said gap through which the fluid or vapor may pass whereby fluid or vapor to be tested may move through each of said gaps between said input and output cables so that light from each of said respective light sources travels through its respective said input cable, through its respective said gap, and through its respective said output cable before impinging on respective said spectrometer.

18. A non-destructive diagnostic device for continuously testing fluid or vapor comprising:
 a) at least two light sources, each of said light sources emitting light at a different preselected wavelength;
 b) means for directing light from each of said light sources through the fluid or vapor;
 c) means for receiving light from each of said light sources after it has been directed through the fluid or vapor, said means for receiving light separated from said means for directing light by a distance, thereby forming a gap through which the fluid or vapor may pass;
 d) means, connected to said means for receiving light, for determining the absolute intensity of light from each of said light sources after is has been directed through the fluid of vapor and passed to said means for determining through said means for receiving, whereby each of said light sources has a corresponding means for directing light, means for receiving light, and means for determining the absolute intensity of light;

e) means for determining the ratio of absolute intensity of light from each of said light sources after the light has been directed through the fluid or vapor;

f) means, responsive to said means for determining, for creating control signal indicating that said ratio is outside of a preselected limit;

g) means, responsive to said control signals, for communicting that said ratio is outside of said preselected limit; and, h) a probe, said probe being insertable into the fluid or vapor to be tested, said means for directing light including respective fiber optic input cables connecting each of said light sources with the fluid or vapor to be tested, said means for receiving light also including respective fiber optic output cables extending from the fluid or vapor to be tested to respective said means for determining the absolute intensity, said input and output cables extending into and out of, respectively, said probe, respective said input and output cables corresponding to each of said light sources, respective said input and output cables being separated from each other within said probe thereby forming said gap, each of said gaps in contact with the fluid or vapor whereby fluid or vapor to be tested may move through each of said gaps between said input and output cables so that ligh from each of said respective light sources travels through its respective said input cable, through its respective said gap, and through its respective said output cable before impining on respective said means for determining the absolute intensity.

19. The device of claim 18 wherein said probe is adapted to be hand-held and manually inserted into the fluid or vapor to be tested.

20. The device of claim 18 wherein said probe comprises:

a) a connector, through which said fiber optic input cables enter said probe and said fiber optic output cables exit said probe;

b) a bulk head, attached to said connector, for positioning said fiber optic input and output cables; and c) a wall placed between respective pairs of fiber optic input and fiber optic output cables so that light emitted from one of said fiber optic input cables is inhibited from being diffracted into another non-corresponding fiber optic output cable.

21. The device of claim 20 wherein said probe further comprises a screen surrounding said fiber optic input and output cables and said wall so that said gap between said fiber optic input and output cables is shielded from debris passing into said gap.

22. A method for non-destructively and continuously testing fluids or vapors for contaminants, the fluid or vapor contained in a fluid or vapor reservoir, the fluid or vapor taken from a group consisting of oil based lubricants, hydraulic oils, brake fluids, transmission fluids, coolant or radiator fluids, organic, carbon based fuel vapors, and organic, carbon based solvent vapors, comprising the steps of:

a) passing light of at least two different wavelengths through the reservoir of fluids or vapors;

b) detecting the light of the different wavelengths after the light has passed through the reservoir;

c) determining the absolute intesntiy of the light of the different wavelengths after the light has been detected;

d) determining the ratio of the determined absolute intensities of the light; and, e) comparing the determined ratio to a preestablished ratio of absolute intensities of the light to determine whether the determined ratio indicates that the condition of the fluid or vapor is outside acceptable values.

23. A non-destructive diagnostic device for continuously testing fluid or vapor comprising:

a) at least two light sources, each of said light sources emitting light at a different preselected wavelength;

b) means for directing light from each of said light sources through the fluid or vapor;

c) means for receiving light from each of said light sources after it has been directed through the fluid or vapor, said means for receiving light separated from said means for directing light by a distance, thereby forming a gap through which the fluid or vapor may pass;

d) means, connected to said means for receiving light, for determining the absolute intensity of light from each of said light sources after it has been directed through the fluid of vapor and passed to said means for determining through said means for receiving, whereby each of said light sources has a corresponding means for directing light, means for receiving light, and means for determining the absolute intensity of light;

e) means for determining the ratio of absolute intensity of light from each of said light sources after the light has been directed through the fluid or vapor;

f) means, responsive to said means for determining, for creating control signals indicating that said ratio is outside of a preselected limit;

g) means, responsive to said control signals, for communicating that said ratio is outside of said preselected limit; and, h) means for modulating said light sources comprising means for alternately pulsing respective said light sources and simultaneously activating the corresponding said means for determining the absolute intensity of light so that light from one light source that is diffracted by the fluid or vapor will impinge on an inactive means for determining the absolute intensity of light corresponding to an inactive said light source.

24. A non-destructive diagnostic device for continuously testing fluid or vapor comprising:

a) at least two light sources, each of said light sources emitting light at a different preselected wavelength;

b) means for directing light from each of said light sources through the fluid or vapor comprising respective input fiber optic cables, said input fiber optic cables receiving light from said light sources at a first end and directing the light through the fluid or vapor at a respective second end;

c) means for receiving light from each of said light sources after it has been directed through the fluid or vapor comprising respective output fiber optic cables, each having a first and a second end, respective said output fiber optic cables each receiving light directed through the fluid or vapor from respective said input fiber optic cables at said first end, respective said input fiber optic cables separated from respective said output fiber optic cables by a distance thereby forming a gap through which the fluid or vapor may pass;

d) means, connected to said second end of respective said output fiber optic cables, for determining the absolute intensity of light from each of said light sources after the light has been directed through the fluid of vapor, said means for determining comprising a spectrometer, whereby each of said light sources has a corresponding means for directing light and a means for receiving light;

e) means for determining the ratio of absolute intensity of light from each of said light sources after the light has been directed through the fluid or vapor, comprising an analog divider;

f) means, responsive to said means for determining, for creating control signals indicating that said ratios are outside of a preselected limits;

g) means, responsive to said control signals, for communicating that said ratios are outside of said preselected limits; and, h) a probe, said probe being insertable into the fluid for vapor to be tested, said probe enclosing respective said send ends of said input fiber optic cables and said first end of said output fiber optic cables, said second end of said input fiber optic cables and said first end of said output fiber optic cables being separated thereby forming said gap through which the fluid or vapor may pass whereby fluid or vapor to be tested may move through each of said gaps between said input and output cables so that light from each of said respective light sources travels through its respective said input cable, through its respective said gap, and through its respective said output cable before impinging on respective said spectrometer.

25. A non-destructive diagnostic device for continuously testing fluids or vapors for contaminants, said fluids or vapors contained in a fluid or vapor reservoir, the fluid or vapor taken from a group consisting of oil based lubricants, hydraulic oils, brake fluids, transmission fluids, coolant or radiator fluids, organic, carbon based fuel vapors, and organic carbon based solvent vapors, comprising:

a) means for passing light of at least two different wavelengths through the reservoir of fluids or vapors;

b) means for detecting the light of the different wavelengths after the light has passed through the reservoir;

c) means for positioning said means for passing light and said means for detecting the light in the reservoir, said means for receiving light separated from said means for directing light by a distance, thereby forming a gap through which the fluid or vapor may pass;

d) means for determining the absolute intensity of the light of the different wavelengths after the light has been detected;

e) means for determining the ratio of the determined absolute intensities of the light; and, f) means for comparing the determined ratio to a preestablished ratio of absolute intensities of light to determine whether the determined ratio indicates that the condition of the sample is outside acceptable values;

wherein said device operates according to the following steps:

g) passing light of at least two different wavelengths, from said means for passing light, through fluid or vapor;

h) detecting the light of the different wavelengths, by said means for detecting light, after the light has passed through the fluid or vapor; p1 i) determining the absolute intensity of the light of the different wavelengths, by said means for determining the absolute intensity of the light, after the light has been detected by said means for detecting;

j) determining the ratio of the determined absolute intensities of the light by said means for determining the ratio; and, k) comparing the determined ratio, by said means for determining, to a preestablished ratio of absolute intensities of light to determine whether the determined ratio indicates that the condition of the sample is outside acceptable values.

26. A non-destructive diagnostic device for continuously testing oil based lubricants contained in a reservoir, comprising:

a) means for passing light of at least two different wavelengths through the reservoir of oil based lubricants, said wavelengths including 450 nanometers and 550 nanometers;

b) means for detecting the light of the different wavelengths after the light has passed through the oil in the reservoir;

c) means for positioning said mean for passing light and said means for detecting the light in the reservoir, said means for detecting the light separated from said means for passing light by a distance, thereby forming a gap through which the oil based lubricant may pass;

d) means for determining the absolute intensity of the light of the different wavelengths after the light has been detected;

e) means for determining the ratio of the determined absolute intensities of the light; and, f) means for comparing the determined ratio to a preestablished ratio of absolute intensities of light to determine whether the determined ratio indicates that the condition of the sample is outside acceptable values.

* * * * *